United States Patent
Van Kooten et al.

[11] Patent Number: 6,100,093
[45] Date of Patent: Aug. 8, 2000

[54] METHOD AND SYSTEM FOR DETERMINING THE QUALITY OF A CROP

[75] Inventors: Olaf Van Kooten; Jeremy Harbinson, both of Wageningen, Netherlands

[73] Assignee: Instituut Voor Agrotechnologisch Onderzoek (ATO-DLO), Wageningen, Netherlands

[21] Appl. No.: 09/171,007
[22] PCT Filed: Apr. 9, 1997
[86] PCT No.: PCT/NL97/00182
§ 371 Date: Oct. 9, 1998
§ 102(e) Date: Oct. 9, 1998
[87] PCT Pub. No.: WO97/39350
PCT Pub. Date: Oct. 23, 1997

[30] Foreign Application Priority Data

Apr. 15, 1996 [NL] Netherlands ............................ 1002870

[51] Int. Cl.[7] ............................ G01N 21/63; G01N 33/48
[52] U.S. Cl. ........................... 436/34; 436/35; 436/164; 436/905; 422/82.09; 435/288.7; 356/432
[58] Field of Search ........................ 422/82.09; 436/20, 436/34, 35, 164, 905; 435/288.7; 356/432, 433, 434

[56] References Cited

U.S. PATENT DOCUMENTS

| | | | |
|---|---|---|---|
| 4,942,303 | 7/1990 | Kolber et al. | 250/458.1 |
| 5,012,609 | 5/1991 | Ignatius et al. | |
| 5,602,446 | 2/1997 | Kolber et al. | 315/241 P |
| 5,854,063 | 12/1998 | Li et al. | 435/287.1 |

FOREIGN PATENT DOCUMENTS

| | | |
|---|---|---|
| 42 32 281 | 3/1994 | Germany . |
| 44 27 438 | 2/1996 | Germany . |

OTHER PUBLICATIONS

N.G. Bukhov et al., "Analysis of dark–relaxation kinetics of variable fluorescence in intact leaves", *Chemical Abstracts*, vol. 116, No. 25, Jun. 22, 1992.

W.P. Quick et al., "An examination of factors contributing to non–photochemical quenching of chlorophyll fluorescence in barley leaves", *Chemical Abstracts*, vol. 112, No. 9, Feb. 26, 1990.

B. Genty et al., "The relationship between nonphotochemical quenching of chlorophyll fluorescence and the rate of photosystem 2 photochemistry in leaves", *Chemical Abstracts*, vol. 113, No. 23, Dec. 3, 1990.

*Primary Examiner*—Jeffrey Snay
*Attorney, Agent, or Firm*—Young & Thompson

[57] ABSTRACT

The invention relates to a method for determining the quality of a crop, comprising the determination of at least one characteristic parameter of the photosynthesis process of the crop, which parameter serves as a quality indicator for the crop, wherein the parameter belongs to the photosystem I (PSI), which is known per se, and wherein the determination of the parameter comprises the following steps: (a) bringing at least some of a number of types of molecules which are located on the donor side of PSI into an oxidised state; (b) allowing at least some of the oxidised molecules to be reduced; and (c) determining a relaxation parameter which contains information on the rate of the reduction, wherein step (c) comprises at least the following sub-steps: (1) measurement of absorption of light in a predetermined wavelength region by the oxidised molecules in the crop during the reduction, and (2) calculation of a rate parameter which contains information on the rate of a change in the measured absorption as a function of time, the rate parameter being the relaxation parameter. The invention also relates to a system for determining a quality indicator for a crop on the basis of the relaxation parameter obtained using the said method.

13 Claims, 2 Drawing Sheets

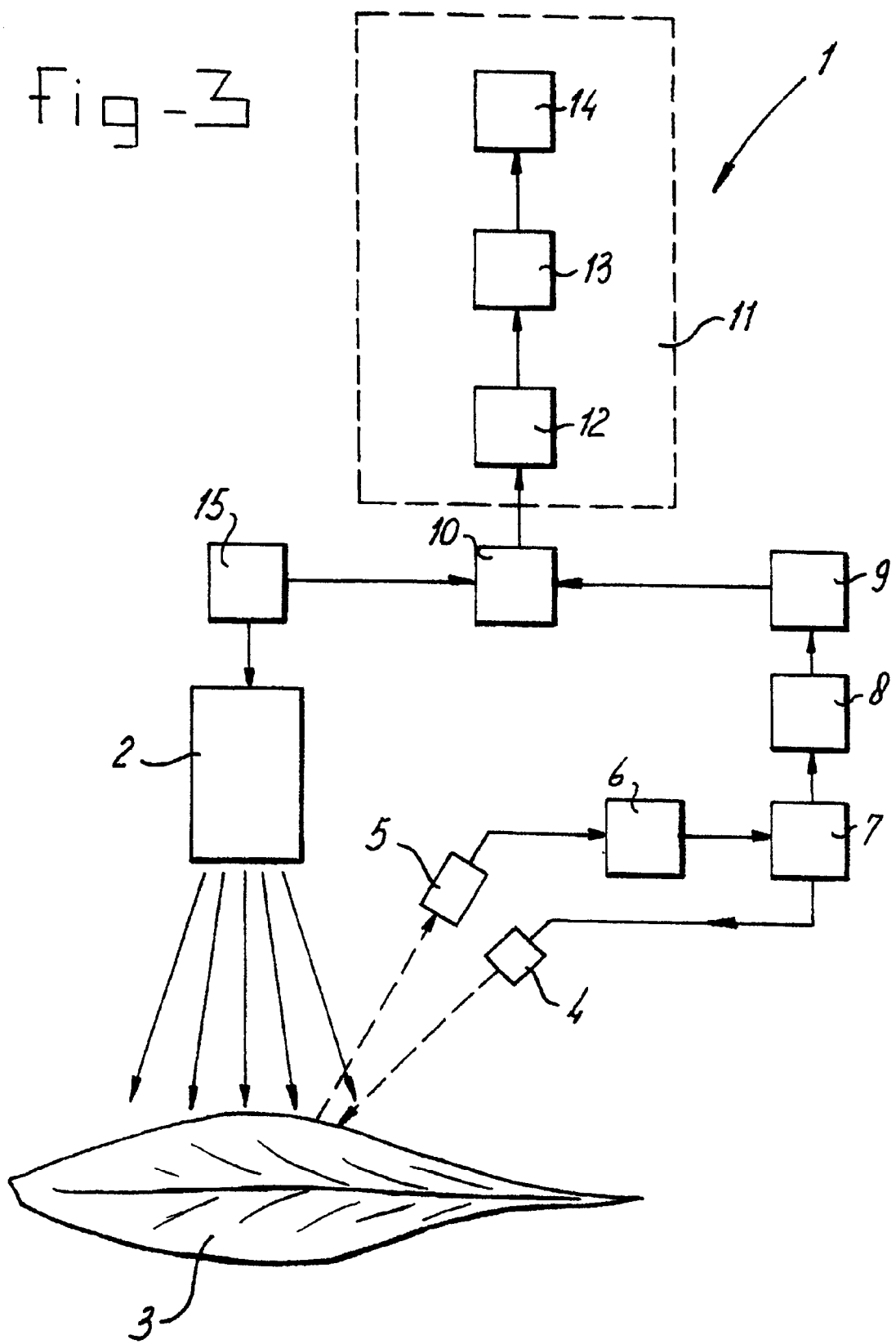

METHOD AND SYSTEM FOR DETERMINING THE QUALITY OF A CROP

The invention relates to a method for determining the quality of a crop, comprising the determination of at least one characteristic parameter of the photosynthesis process of the crop, which parameter serves as a quality indicator for the crop.

Crops, such as plants and flowers, but also vegetables and fruit, use a photosynthesis process to draw from their environment the energy they need to survive. It is pointed out that hereinafter the term "crops" is used to designate both the crops in the field and the products harvested therefrom. During the abovementioned photosynthesis process, carbon dioxide is converted with the aid of sunlight into hydrocarbon compounds, during which process oxygen is also liberated. Every crop is equipped with its own photosynthesis system for this purpose, which system is located in the green parts of the crop, such as the leaves, the stem or the fruit. A photosynthesis system of this type is, inter alia, provided with a light-intercepting system which contains two important pigment-protein complexes, namely the photosystems I and II (PSI and PSII, respectively), which are equipped with photon transfer components. With the aid of its light-intercepting system, a crop absorbs sunlight. Said sunlight provides, inter alia, for a chain of successive oxidation/reduction reactions of components in the photosynthesis system, the intercepted solar energy being transported by the photon transfer components essentially to PSI and to PSI. The transported solar energy is then used to produce a photochemical reaction in the crop, during which electrons are transported and oxygen is liberated.

A method of the type mentioned in the preamble is disclosed in the article entitled "Determination of the physiological state of potted plants and cut flowers by modulated chlorophyll fluorescence" by O. van Kooten et al. in Acta Horticulturae 298, 1991. With the known method the efficiency of the linear stream of electrons in the photosynthetic membranes of potted plants and cut roses is determined in vivo. To this end, the fluorescence production F of the chlorophyll molecules which form part of PSII is first of all measured in a specific wavelength region under normal intensity of the ambient light. The maximum fluorescence production $F_m$ of the chlorophyll molecules is then measured in the same wavelength region at a saturating intensity of the ambient light. With the known method a first activating light source with adjustable light intensity and a second measuring light source of constant light intensity are used. Both light sources transmit light in a first wavelength region which comprises wavelengths between about 350 and 700 nm. After a set period has elapsed, the chlorophyll fluorescence is then detected in a second wavelength region between 700 and 730 nm. Since fluorescence per se signifies loss of the solar energy intercepted by the crop, the detected fluorescence productions F and $F_m$ can then be used to calculate the efficiency of the linear stream of electrons. This parameter can be used in accordance with the known method as a quality indicator for the crop.

The known method has the disadvantage that the value of the parameter determined by said method is highly dependent on, in particular, the intensity of the ambient light. Other ambient conditions, such as the temperature and the gas composition and the degree of relative humidity of the air, also influence the value of the parameter. A correction must first be made for all of these factors before the parameter determined using the known method is usable as an absolute quality indicator. In order to reduce the influence of these environmental factors, the crop must, moreover, preferably be screened from the environment as far as possible while carrying out the method. This demands the use of a supplementary, complex and therefore expensive screening device.

The aim of the present invention is to overcome the abovementioned disadvantage and to provide a method of the type mentioned at the start with which an absolute quality indicator for a crop can be determined in vivo in a reliable manner.

To this end, the method according to the present invention is characterised in that the parameter belongs to the photosystem I (PSI), which is known per se, and in that the determination of the parameter comprises the following steps:

(a) bringing at least some of a number of types of molecules which are located on the donor side of PSI into an oxidised state;
(b) allowing at least some of the oxidised molecules to be reduced, and;
(c) determining a relaxation parameter which contains information on the speed of the reduction, wherein step (c) comprises at least the following sub-steps:
  (1) measurement of absorption of light in a predetermined wavelength region by the oxidised molecules in the crop during the reduction, and
  (2) calculation of the rate of change in the measured absorption as a function of time, the rate parameter being the relaxation parameter.

At the donor side of PSI there is a triplet of molecules linked in series, specifically P-700, plastocyanin and cytochrome-f. The reduction of the donor side of PSI constitutes the slowest link in the chain of oxidation/reduction reactions of photosynthetic electron transport. The relaxation rate of said redox reaction is regulated by the need of the entire crop for photosynthetic metabolites and is consequently a criterion for the relaxation rate of the entire photosynthesis process of the crop. Said relaxation rate is characterised by a relaxation parameter, the value of which is light-independent. The relaxation parameter can therefore be used as an absolute quality indicator for the crop, without this necessitating correction, during measurement on the crop, for the ambient conditions normal for the crop.

In the method according to the invention, the step of determination of such a relaxation parameter comprises at least the sub-steps of (1) measurement of absorption of light in a predetermined wavelength region by the oxidised molecules of the crop during the reduction, and (2) the calculation of a rate parameter which contains information on the speed of a change in the measured absorption as a function of time, the rate parameter being the relaxation parameter. The use of this measurement technique makes it possible to measure a process in the crop which has dynamics of a few kHz or even higher. This measurement technique is outstandingly suitable for measurement of the abovementioned relaxation parameter, since characteristic values for, for example, the rate constants for the reduction of oxidised molecules from the abovementioned triplet are in general of the order of magnitude of from a few Hz to several kHz.

On the grounds of the dynamics of the reduction process, which have been described above, it will be clear that the method according to the invention also offers the advantage that a quality indicator for the crop, in the form of a relaxation parameter, can be determined virtually in real time using this method.

In a preferred embodiment at least some of the molecules are oxidised with the aid of light in a first wavelength region, the first wavelength region essentially comprising wavelengths of between 350 and 700 nm. In this embodiment the number of oxidised molecules is increased with the beneficial consequence that it will be possible to measure a greater absorption signal.

In a further preferred embodiment the change in absorption is measured with light in a wavelength region which essentially comprises wavelengths of between 800 and 850 nm. Light of such a wavelength is advantageously absorbed virtually exclusively by the molecules of the triplet when the latter are in the oxidised state but are not used for photosynthetic electron transport. With light in this wavelength region, the change in absorption can therefore be measured with an improved signal/noise ratio because the measurement light intensity can be high without this influencing the electron transport.

The invention also relates to an apparatus for determining a quality indicator for a crop on the basis of the relaxation parameter obtained using the abovementioned method, which apparatus is provided with:
(a) means for bringing at least some of a number of types of molecules which are located on the donor side of PSI into an oxidised state;
(b) means for allowing at least some of the oxidised molecules to be reduced, and;
(c) means for determining a relaxation parameter which contains information on the speed of the reduction, wherein the means for determining a relaxation parameter comprise at least:
  (1) means for measurement of absorption of light in a predetermined wavelength region by the oxidised molecules in the crop during the reduction, and
  (2) means for calculation of a rate parameter which contains information on the speed of a change in the measured absorption as a function of time, the rate parameter being the relaxation parameter. Said apparatus can be reliably and advantageously implemented with the aid of software. The use of software also offers the possibility of a virtual real-time determination of a quality indicator for the crop.

The present invention will be explained in detail below with reference to the accompanying drawing, in which:

FIG. 3 shows a block diagram of a preferred embodiment of an apparatus according to the present invention.

Figure 1:
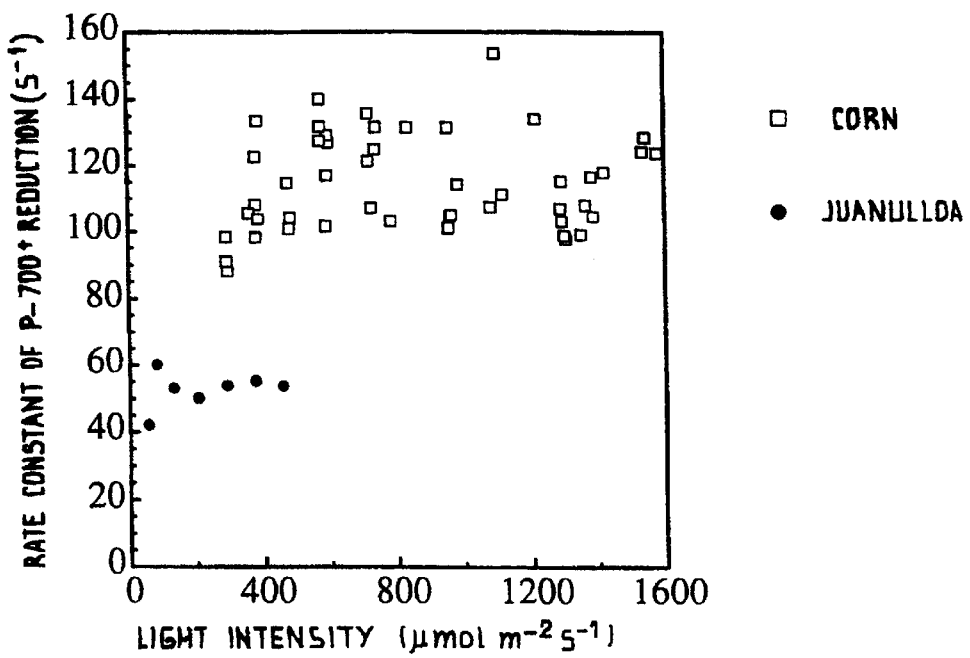
FIG. 1 shows a plot of the rate constant for, essentially, reduction of P-700$^+$ reaction centres against the light intensity.

FIG. 1 shows the plot of the rate constant for, essentially, reduction of P-700$^+$ reaction centres against the light intensity for two different crops, i.e. maize and juanulloa. The values shown for the rate constant were calculated on the basis of changes in absorption which were measured with light of a wavelength of essentially 820 nm. It can clearly be seen from FIG. 1 that the said rate constant is approximately independent of the prevailing light intensity. This surprising result was found to be valid for many types of crops, as has been demonstrated on the basis of further experimental research by the Applicant. It has also been found from the experiments that the light-independence of the rate constant applies in general to changes in absorption which were measured for light of a wavelength in the range between 690 and 1100 nm. Light having such a wavelength range is readily absorbed by two of the three abovementioned molecules from the triplet on the donor side of PSI, namely P-700 and plastocyanin, when said molecules are in the oxidised state.

Figure 2:
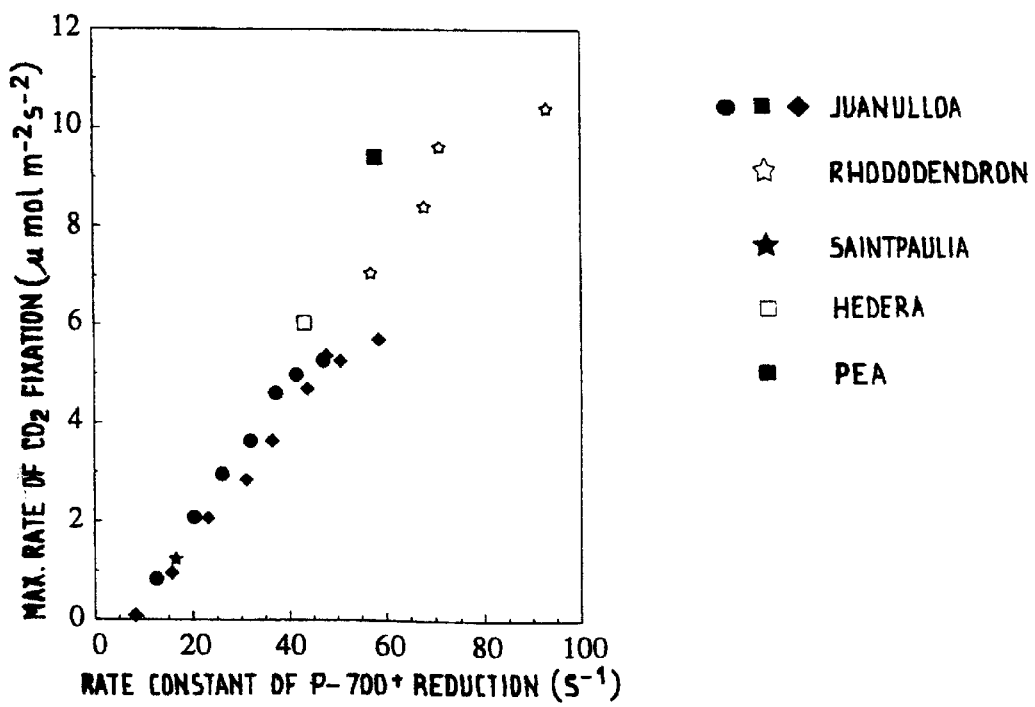
FIG. 2 shows a plot of the maximum rate of CO$_2$ fixation against the rate constant for, essentially, P-700$^+$ reduction for five different crops.

FIG. 2 shows a plot of the maximum rate of CO$_2$ fixation against the rate constant for P-700$^+$ reduction for five different crops. Once again the values shown for the rate constant were calculated on the basis of measured changes in absorption with light having essentially a wavelength of 820 nm. The measurements were carried out at an ambient temperature of 20° C. and an oxygen concentration of 2%. The five crops are juanulloa, rhododendron, saintpaulia, hedera and peas. It can be deduced from FIG. 2 that the rate constant for essentially P-700$^+$ reduction and the maximum rate for CO$_2$ fixation show a linear dependence. Said dependence can be approximately described by means of the following equation:

$$y = a\,K_e - b \tag{1}$$

where y is the maximum rate for CO$_2$ fixation and $K_e$ is the rate constant for P-700$^+$ reduction. Approximately, $0.07 < a < 0.21$ and $0.5 < b < 1.5$, in which context the precise values for a and b will depend mainly on the oxygen concentration. For the comparison shown in FIG. 2, $a = 0.143$ and $b = 1.018$. Equation (1) is valid for many varieties of crops and is wavelength-independent, as has been found from various experiments.

It is a fact known from practice that the maximum rate at which a crop is able to bind CO$_2$ is an indication for the physiological condition of the crop. This can easily be understood when it is realised that during the photosynthesis process, which has been described above as the most vital process for a crop, carbon dioxide is converted to hydrocarbon compounds and oxygen in accordance with the following equation:

$$CO_2 + H_2O \rightarrow (CH_2O) + O_2 \tag{2}$$

It was the surprising results discussed above, which are shown in FIGS. 1 and 2, which gave rise to the concept of the invention, namely to determine the quality of a crop on the basis of a relaxation parameter which contains information on the rate of reduction from an oxidised state of at least some of a number of types of molecules which are located on the donor side of PSI. The most important advantage of the use of said relaxation parameter as a quality indicator is that the value thereof can be determined independently of the intensity of the ambient light.

According to the invention, determination of the relaxation parameter comprises at least measuring absorption of light in a predetermined wavelength region by the crop to determine the relaxation parameter from a change in absorption as a function of time. The most important advantage of the use of said measurement technique is that said technique is suitable for real-time applications. Moreover, said measurement technique can be implemented in a reliable manner in the form of a compact system using means known per se.

In a preferred embodiment of the method according to the invention, the relaxation parameter is determined for reduction of one or more of the abovementioned molecules from their oxidised state in a number of steps. In the first step at least some of the molecules are oxidised with the aid of light of a wavelength in a first predetermined wavelength region. Preferably, the light has a predetermined wavelength of between 350 and 700 nm. The absorption of light of a wavelength in a second predetermined wavelength region by the oxidised molecules is then measured over a predetermined period. Said second predetermined wavelength is preferably between 690 and 1100 nm. More preferentially, said wavelength is between 800 and 850 nm and is, for example, 820 nm. The change in absorption measured with measurement light of a wavelength of 820 nm is designated below as $\Delta A_{820}$.

The measured absorption will change with time as a result of naturally occurring reduction of the oxidised molecules. The decrease in the absorption signal shows, approximately, a mono-exponential behaviour in accordance with the equation $$A(t) = e^{-K_e t} \tag{3}$$

where $A(t)$ is the absorption at time t and $K_e$ is the associated characteristic rate constant which is a criterion for the rate of reduction. On the basis of the change in absorption as a function of time, which has been described above, the associated rate constant for the reduction is then calculated in a third step of the method according to the invention. As an alternative for the rate constant, it is, of course, also possible to determine a different rate parameter, such as the half-life.

Preferably, the measurement light has a wavelength of approximately 820 nm. At this wavelength essentially 60% of the measured change in absorption is caused by reduction of oxidised P-700 molecules, that is to say special chlorophyll-a molecules which form the reaction centre of PSI. Optionally, the rate constant associated with $\Delta A_{820}$ can be used to determine the maximum rate for $CO_2$ fixation for the crop with the aid of equation (1), which maximum rate for $CO_2$ fixation also can be used as a quality indicator for the crop concerned.

Per crop it is possible, on the basis of a complete series of conducted experiments, to link a quality indicator to the relaxation parameter determined by the method according to the invention. Said quality indicator could relate to a characteristic of a specific crop which is important to the consumer. For roses, for example, opening of the flower bud in the vase can be chosen as a quality characteristic. On the basis of experiments which have already been carried out, it is found that a rose virtually always opens properly with a rate constant for $\Delta A_{820}$ greater than 100 $s^{-1}$. At a rate constant for $\Delta A_{820}$ of less than 40 $s^{-1}$ a rose will certainly not open and the flower will start to droop within a few days. With a rate constant in the intermediate range, the rose will partially open. In this example, therefore, three quality ranges can be indicated which are directly related to the rate constant which can be determined with the aid of the method according to the invention which has been described above. The rate constants in this example were determined at a temperature of 20° C. on the leaves of roses which had been in water for at least two hours.

The quality criterion to be chosen will differ per crop. In the case of cucumber, for example, the reduction in the chlorophyll content in the skin can be taken as a quality criterion. The darker green the cucumber, the higher is the quality class. The rate at which the cucumber "becomes paler" under standard conditions is a criterion for the life thereof.

Analogously to the above example, here again three quality ranges can be indicated for which the limits are determined by the respective rate constants 100 $s^{-1}$ and 50 $s^{-1}$. The rate at which the cucumber discolours will be lower, the higher the rate constant.

In the case of pot plants such as calceolaria, the quality can be expressed as the time which elapses before the plant is no longer saleable. In this example, a rate constant of 75 $s^{-1}$ is very good and a value of 20 $s^{-1}$ very poor.

The quality indicator chosen can, as an alternative, also relate to a characteristic of the crop which is important to the producer. For instance, it is possible to choose the stage of development of a crop as the quality criterion in order, for example, to determine the optimum harvesting time for a crop, for example a fruit, such as apples and bananas, on the basis of this criterion. Experiments have shown that the relaxation parameter follows an optimum curve which is related to the stage of development or the ripeness of the crop to be harvested. In general, a relaxation parameter value which precedes the relaxation parameter value associated with the optimum for the curve will indicate a suitable harvesting time. How far the relaxation parameter value must precede this "optimum value" is dependent on, inter alia, the expected transport time, in connection with after-ripening. Furthermore, the stage of development of a potato can, for example, be used to determine the most suitable point in time for killing the tops by spraying or by beating prior to lifting. In this example a relaxation parameter value (measured on the tops) which is just beyond the said "optimum value" will indicate the optimum point in time for this.

On the basis of the above, quality ranges can be defined for each crop with respect to a preselected quality criterion. The relaxation parameter which has been determined for the crop then indicates the current quality range of the crop concerned. The relaxation parameter can optionally be corrected for temperature in a manner which will be explained further below. Provided the carbon dioxide concentration varies within normal values (i.e. a $CO_2$ concentration of between 300 and 700 ppm by volume), it will not actually affect the determination of the relaxation parameter.

On the basis of the above it is possible, for example, to compile a database for each crop in which different values or ranges for the relaxation parameter are related to a quality indicator. In a preferred embodiment of the method according to the invention, this database can be used to determine a quality indicator for the crop on the basis of the relaxation parameter determined. To this end, said method comprises the following steps:

comparison of the relaxation parameter determined with one or more relaxation parameters or relaxation parameter ranges for the crop which are stored in a database; and searching in the database for the quality indicator associated with a relaxation parameter or relaxation parameter range, stored in the database, which essentially corresponds to the relaxation parameter determined.

FIG. 3 shows a preferred embodiment of a system for carrying out the method according to the invention. System 1 comprises a first light source 2 for emitting light in a first wavelength region, which is suitable for oxidising at least some of the said molecules on the donor side of PSI in the crop concerned. A leaf 3 of the crop is shown diagrammatically. The first light source 2 preferably emits light with a wavelength of between 400 and 700 nm. More preferentially, the light is emitted in the form of a brief flash. The duration of such a flash is preferably about 1 ms. As a result of such a light flash, at least some of the said molecules present in leaf 3 will oxidise. Said molecules in the oxidised state display an absorption behaviour which differs from that of the non-oxidised molecules with respect to light in a second wavelength region which comprises wavelengths between 690 and 1100 nm. Said light is supplied by a second light source 4. More preferentially, the light from the second light source 4 has a wavelength of between 800 and 850 nm, for example 820 nm. Light of such a wavelength is readily absorbed by the oxidised molecules in leaf 3. Following absorption, the oxidised molecules will then reduce naturally as a consequence of the photosynthesis process. As a result the absorption signal for light in the second predetermined wavelength region will decrease over time. As has already been described above, said decrease in absorption displays approximately a mono-exponential behaviour and can therefore be characterised on the basis of a rate constant or another rate parameter, such as a half-life. Detection means 5 are provided for measurement of the absorption, which detection means are equipped to detect changes in the intensity of the light of the second wavelength region transmitted or scattered by leaf 3. In the embodiment shown, the detection means 5 are positioned such that said means collect the light scattered by leaf 3.

Light source 4 is preferably an infrared light-emitting diode, which optionally can be provided with a filter. It is important that the output signal from the second light source 4 is very stable, because the changes in absorption which are to be measured are very small (of the order of magnitude of $10^4$) In the preferred embodiment shown, the light from light source 4 is modulated by modulator/demodulator 7. The modulated light is easier to detect by detection means 5, interference by other light in the same wavelength region being excluded as far as possible. The modulation is preferably an amplitude modulation. The modulation frequency must be high enough to make it possible to filter and/or to demodulate the signal to be detected, which signal is proportional to the intensity of the light beam originating from light source 4, it still being possible to determine the small changes in absorption signal which take place within a few milliseconds. The modulation frequency required depends on various factors, but is preferably 20 kHz or higher.

Detection means 5 preferably comprise one or more photodiodes, for example silicon diodes. Optical filters can be used to make the detection means 5 more sensitive to the wavelength region concerned, within which the changes in absorption take place. Said optical filters can comprise coloured glass (for example Schott RG 9 or RG 780) or can be of the thin-film type. Since silicon photodiodes produce low-power signals, said signals are preferably first amplified before they are further processed. For this purpose use can be made of a standard pre-amplifier 6. It will be clear that the frequency characteristic of the combination of detection means 5 and preamplifier 6 must be suitable for detection of the amplitude-modulated light which is scattered by leaf 3 in the frequency domain. The absorption signal detected with the aid of detection means 5 is then first demodulated in modulator/demodulator 7.

The demodulated signal is then fed to filter means 8 to remove undesired noise components. Standard filter means, such as a low-permeability filter, can be used. In the embodiment of system 1 shown, subtraction means 9 are also provided with which the standard absorption signal of leaf 3 at the relevant wavelength, for example 820 nm, is subtracted from the measured absorption signal. In this way the absorption difference which is caused by reduction of the said oxidised molecules (i.e. the signal of interest) is differentiated more clearly. By way of illustration of the magnitude of the absorption difference signal, complete oxidation of all P-700 reaction centres present in a characteristic crop, for example, results in a change in the intensity of a scattered light beam from 5 000 mV to 4 975 mV. The signal processed in this way can be saved in memory 10 for further processing.

In the preferred embodiment shown, system 1 also comprises a system 11 for determination of a quality indicator on the basis of the change in absorption over time which has been detected by detection means 5 and has also been processed with the aid of the signal-processing means described above. The system 11 is provided with computing means 12 for calculating the relaxation parameter, such as the rate constant, associated with the change in the absorption over time. The system 11 also comprises comparison means 13 for comparing the calculated relaxation parameter with one or more relaxation parameters or relaxation parameter ranges for the crop which have been stored in a database, as described above. The system 11 also comprises search means 14 for searching for the quality indicator associated with a relaxation parameter or relaxation parameter range, stored in the database, which essentially corresponds to the calculated relaxation parameter. The system 11 can optionally be provided with correction means (not shown) for correcting the relaxation parameter to take account of ambient conditions during the determination of the change in absorption. Ambient conditions, such as temperature or $O_2/CO_2$ concentration, on the basis of which, for example, a correction factor for the relaxation parameter can be determined, must then have been measured during the experiment. Preferably, the correction means are equipped for recalculating the relaxation parameter to give a relaxation parameter at a standard temperature, making use of the body temperature of the crop. Experiments have shown that, for example, the said rate constant according to an optimum curve depends on the temperature of the crop during the absorption measurement. The temperature at which the rate constant is maximum can diverge somewhat for different crops. Furthermore, it has been found that the rate constant measured at a temperature which deviates appreciably from the optimum temperature can be a factor of 4 to 5 lower than the maximum value for the rate constant. However, the change in rate constant as a function of temperature is essentially the same for all crops. The temperature correction can therefore, for example, be carried out on the basis of a single model for all crops. It is also conceivable to include the temperature in the abovementioned database. The quality indicator can then be determined on the basis of the temperature value and the value of the relaxation parameter.

Finally, in the preferred embodiment shown light source 2 is coupled to actuation means 15. Said actuation means are advantageously connected to memory 10 to issue a start signal at the start of a measurement. Such a start signal can, for example, be given after completion of a light flash by light source 2, memory 10 automatically saving the signals originating from the detection means 5 after it has received the start signal.

The components 6 to 15 described above are preferably as far as possible constructed in the form of one or more hardware components, such as microprocessors, which are controlled by appropriate software. Said preferred embodiment has the advantage that the system will be very compact and will have a high degree of reliability without demanding particularly extensive maintenance. Moreover, the calculation, comparison and search steps can then be carried out virtually in real time.

In a further preferred embodiment, the system 1 comprises positioning means for positioning the system in the vicinity of the green parts, such as the leaves and the stem, of the crop. Preferably, the positioning means comprise clamping means (not shown) by means of which the system can be clamped to the crop. Light source 2 and/or 4 is/are preferably arranged in said clamping means in the form of light-emitting diodes. The one or more light sources is/are brought into a fixed position with respect to the crop by clamping the system with the aid of the clamping means to one of the leaves or the stem of the crop. The system described above can be constructed in a compact format, so that a user can easily carry it by hand.

For a person skilled in the art it is clear that numerous variants of the embodiments described above are possible. Thus, for example, light source 2 can optionally be omitted from the system 1 as shown in FIG. 3. In that case there is, however, a need for an alternative measure for oxidation of the said molecules. One example of such a measure is to ensure that the crop receives virtually no further light. In that case virtually all of the oxidised molecules of the said type which are present will reduce naturally. The characteristic relaxation parameter associated with this reduction can then, once again, be determined by assuming a mono-exponential behaviour. When calculating the associated rate constant, it is also possible to choose an "oscillator" approach as an alternative to the "mono-exponential" approach described. In the case of the "oscillator" approach, each molecule is regarded as an oscillator, oxidisation of which is triggered by a light pulse and reduction of which is triggered by electron transport. It would then be possible to calculate the rate constant for electron transport by analysis of the frequency characteristic of the amplitude and the phase of the absorption signal as a function of time at a predetermined wavelength, for example 820 nm, in a crop which is exposed to modulated actinic illumination.

Furthermore, as an alternative to the database, described above, in which relaxation parameters or ranges thereof are related to quality indicators, use can be made of an algorithm for calculation of a quality indicator on the basis of the relaxation parameter determined.

Possibly superfluously, it is pointed out that the present invention is not restricted to the embodiments described and illustrated but relates to any embodiment which is consistent with the above description and the appended drawings and which falls within the scope of the appended claims.

Legend for figures

FIG. 1
Ordinate: rate constant for P-700$^+$ reduction (s$^{-1}$)
Abscissa: light intensity ($\mu$mol m$^{-2}$s$^{-1}$)
MAIS=MAIZE FIG. 2
Ordinate: max. rate for CO$^2$ fixation ($\mu$mol m$^{-2}$s$^{-2}$)
Abscissa: rate constant for P-700$^+$ reduction (s$^{-1}$)
RODODENDRON=RHODODENDRONS
ERWT=PEAS

What is claimed is:

1. Method for determining the quality of a crop, comprising the determination of at least one characteristic parameter of the photosynthesis process of the crop, which parameter serves as a quality indicator for the crop, characterised in that the parameter belongs to the photosystem I (PSI), which is known per se, and in that the determination of the parameter comprises the following steps:
    (a) bringing at least some of a number of types of molecules which are located on the donor side of PSI into an oxidised state;
    (b) allowing at least some of the oxidised molecules to be reduced, and;
    (c) determining a relaxation parameter which contains information on the speed of the reduction, wherein step (c) comprises at least the following sub-steps:
        (1) measurement of absorption of light in a predetermined wavelength region by the oxidised molecules in the crop during the reduction, and
        (2) calculation of the rate of change in the measured absorption as a function of time, the rate parameter being the relaxation parameter.

2. Method according to claim 1, wherein step (a) comprises the oxidation of at least some of the molecules with the aid of light in a first wavelength region, the first wavelength region essentially comprising wavelengths of between 350 and 700 nm.

3. Method according to claim 1, wherein step (c1) comprises measurement of the absorption of light in a second wavelength region by the oxidised molecules during a predetermined period, the second wavelength region essentially comprising wavelengths of between 690 and 1100 nm.

4. Method according to claim 3, wherein the second wavelength region essentially comprises wavelengths of between 800 and 850 nm.

5. Method according to claim 3, wherein the relaxation parameter is the rate constant for the reduction and wherein the method further comprises the step of determining the maximum rate of CO$_2$ fixation in the crop on the basis of the rate constant in accordance with the equation:

$$y = a\, K_e - b$$

where y is the rate for CO$_2$ fixation and $K_e$ is the rate constant and wherein, approximately, $0.07 < a < 0.21$ and $0.5 < b < 1.5$.

6. Method according to claim 1, wherein the method further comprises the step of determining a quality indicator on the basis of the relaxation parameter, which further step comprises the following steps:
    comparison of the relaxation parameter determined with one or more relaxation parameters or relaxation parameter ranges for the crop which are stored in a database; and
    searching in the database for the quality indicator associated with a relaxation parameter or relaxation parameter range, saved in the database, which essentially corresponds to the relaxation parameter determined.

7. Apparatus for determining the quality of a crop, comprising the determination of at least one characteristic parameter of the photosynthesis process of the crop, which parameter serves as a quality indicator for the crop, characterised in that the parameter belongs to the photosystem I (PSI), which is known per se, and in that the apparatus comprises:
    (a) means (2) for bringing at least some of a number of types of molecules which are located on the donor side of PSI into an oxidised state;
    (b) means (4) for allowing at least some of the oxidised molecules to be reduced, and;
    (c) means for determining a relaxation parameter which contains information on the speed of the reduction, wherein the means for determining a relaxation parameter comprise at least:
        (1) means (4, 5) for measurement of absorption of light in a predetermined wavelength region by the oxidised molecules in the crop during the reduction, and
        (2) means (12) for calculation of the rate of change in the measured absorption as a function of time, the rate parameter being the relaxation parameter.

8. Apparatus according to claim 7, characterised in that the means for determining a relaxation parameter further comprises:
    comparison means (13) for comparing the relaxation parameter with one or more relaxation parameters or relaxation parameter ranges, stored in a database, for the crop; and
    search means (14) for searching in the database for the quality indicator associated with a relaxation parameter, or relaxation parameter range essentially corresponding to the relaxation parameter, stored in the database.

9. Apparatus according to claim 8, wherein the apparatus is further provided with correction means for correcting the relaxation parameter to take account of ambient conditions during measurement of the absorption.

10. Apparatus according to claim 9, wherein the correction means are equipped for recalculating the relaxation parameter to give a relaxation parameter at a standard temperature, making use of the body temperature of the crop.

11. Apparatus according to claim 7, wherein the means for bringing at least some of a number of types of molecules which are located on the donor side of PSI into an oxidised state are formed by a first light source (2) for emitting light in a first wavelength region for oxidising at least some of the said molecules, wherein the first wavelength region essentially comprises wavelengths of between 400 and 700 nm;

the means for allowing at least some of the oxidised molecules to be reduced are formed by a second light source (4) for emitting light in a second wavelength region for reducing the oxidised molecules, wherein the second wavelength region essentially comprises wavelengths of between 680 and 1100 nm;

means (4, 5) for measurement of absorption of light in a predetermined wavelength region by the oxidised molecules in the crop during the reduction are formed by detection means (5) for then measuring the absorption of the light originating from the second light source by the oxidised molecules during a predetermined period.

12. Apparatus according to claim 11, wherein at least one of the light sources comprises a light-emitting diode.

13. Apparatus according to claim 11, wherein the apparatus comprises clamping means which are equipped for fixing to the crop, and wherein at least one of the light sources is mounted on the clamping means.

* * * * *